(12) United States Patent
Nakamura et al.

(10) Patent No.: US 6,245,210 B1
(45) Date of Patent: Jun. 12, 2001

(54) ICE HAVING STERILIZING POWER AND MANUFACTURING METHOD THEREOF

(75) Inventors: Shinichi Nakamura, Osaka; Kunihiko Fukuzuka, Habikino; Yasushi Hanano, Osaka, all of (JP)

(73) Assignee: Omega Co., Ltd. (JP)

( * ) Notice: Subject to any disclaimer, the term of this patent is extended or adjusted under 35 U.S.C. 154(b) by 0 days.

(21) Appl. No.: 09/298,698

(22) Filed: Apr. 23, 1999

(30) Foreign Application Priority Data

Apr. 24, 1998 (JP) .................................................. 10-131390

(51) Int. Cl.[7] .................................................... C02F 1/461
(52) U.S. Cl. ......................... 205/464; 205/741; 205/742; 422/66
(58) Field of Search ..................................... 205/741, 742, 205/464; 422/66

(56) References Cited

U.S. PATENT DOCUMENTS

| 5,474,662 | * | 12/1995 | Miyamae | .............................. | 204/269 |
| 5,476,579 | * | 12/1995 | Choi et al. | ............................ | 205/335 |

FOREIGN PATENT DOCUMENTS

| 60-056908 | * | 4/1985 | (JP) . | | |
| 428438 | | 5/1992 | (JP) | ................................. | C02F/1/46 |
| 7-154895 | | 6/1995 | (JP) . | | |
| 9149 | | 1/1997 | (JP) | ................................. | A23B/4/06 |

* cited by examiner

Primary Examiner—Arun S. Phasge
(74) Attorney, Agent, or Firm—Hayes, Soloway, Hennessey, Grossman & Hage, PC (57) ABSTRACT

Disclosed is ice having a hypohalogenous acid concentration of 10 ppm or more and a melting point of $-0.03°$ C. This ice has sufficient sterilizing power resulting from hypohalogenous acid having the above concentration and can be used in the state of ice for along time due to the above melting point. A method of manufacturing the ice is also disclosed.

4 Claims, 6 Drawing Sheets

ICE HAVING STERILIZING POWER AND MANUFACTURING METHOD THEREOF

BACKGROUND OF THE INVENTION

1. Field of the Invention

The present invention relates to ice having sterilizing power capable of sterilizing harmful germs, etc., and preventing the increase of them to increase a treatment effect in a medical field and preserve foods and drinks and keep their quality fresh in a food industry by using the ice and a method of manufacturing the ice.

2. Description of the Related Art

As proposed by the inventors of the present invention in Japanese Unexamined Patent Publication No. 9-149, there has been used, as a method of manufacturing ice having sterilizing power which will be used in a medical treatment and food preservation, a method of manufacturing ice by electrolyzing seawater or water containing sodium chloride therein to produce hypochlorous acid as hypohalogenous acid and freezing the water.

However, since seawater (sodium chloride concentration: 3.5%) or water in which sodium chloride is dissolved in an amount of about 0.3–3% is electrolyzed in the above conventional method, sodium chloride of a high concentration remains in the water in which hypochlorous acid is produced and when ice is made by freezing the water, the freezing point of the water is dropped by the remaining sodium chloride and the like. Accordingly, there arises a problem that not only a lower temperature is required to make the ice from the water but also the ice obtained by the above method is liable to melt even if it is used at a low temperature and cannot be used as the ice for a long time because the ice is soft and its freezing point is dropped.

To suppress the drop of the freezing point, the inventors of the present invention tried to produce hypochlorous acid by electrolyzing fresh water such as tap water and the like containing sodium chloride in a low concentration by using a platinum-clad-titanium electrode as an anode and make ice by freezing the water as proposed in Japanese Examined Patent Publication No. 4-28438.

In the method of using the platinum-clad-titanium electrode, however, there is a problem that an efficiency for producing hypohalogenous acid by the electrolysis is low and when the fresh water having a low electric conductivity is used, free residual halogen having a concentration sufficient to obtain sterilizing power cannot be obtained because platinum is exfoliated and the titanium electrode is exposed due to a great increase in a voltage imposed between electrodes.

An object of the present invention made in view of the above problems is to provide ice which has a free residual halogen concentration for obtaining sufficient sterilizing power and sodium chloride remaining therein in a low concentration and can be used for a long time as the ice and a method of manufacturing the ice.

SUMMARY OF THE INVENTION

To solve the above problems, ice having sterilizing power of the present invention has a free residual halogen concentration of 10 ppm or more and a melting point of $-0.03°$ C. or higher.

According to the above feature, an excellent sterilizing capability can be obtained by setting the free residual halogen concentration to 10 ppm or more and it can be made difficult for the ice to melt by setting the melting point to $-0.03°$ C. or higher, whereby the ice can be used in the state of ice for a long time.

It should be noted that the free residual halogen concentration means the total concentration of hypohalogenous acid and hypohalogenous acid ion in the present invention.

A method of manufacturing ice having sterilizing power of the present invention comprises the steps of supplying fresh water containing sodium chloride of a low concentration set to 5–500 ppm and approximately similar to tap water to an electrolyzing passage formed between an anode plate and a cathode plate disposed at a prescribed interval with at least the anode plate composed of a ferrite electrode or a graphite electrode; electrolyzing the fresh water and making it to sterilizing water having a prescribed free residual halogen concentration; and making ice by freezing the sterilizing water.

According to the above feature, since hypohalogenous acid is produced by using fresh water containing sodium chloride having a low concentration of 5–500 ppm, the drop of the freezing point of the sterilizing water obtained by the electrolysis can be suppressed to $0.03°$ C. or less. Accordingly, not only the sterilizing water can be easily made to ice by being frozen but also the ice is made difficult to melt, whereby the ice can be used in the state of ice for a long time.

Further, since the anode plate is composed of ferrite or graphite, a high efficiency for producing hypohalogenous acid and hypohalogenous acid ion can be obtained even from the fresh water having the low sodium chloride concentration as compared with the conventional platinum-clad titanium electrode. Accordingly, sterilizing water can be provided with a prescribed free residual halogen concentration capable of obtaining a sufficient sterilizing capability. Since the sterilizing water has the high hypohalogenous acid and hypohalogenous acid ion producing efficiency, the throughput of an electrolyzer can be increased by increasing the flow rate of the water passing through the electrolyzing passage and the cost of the sterilizing water can be reduced.

In the method of manufacturing ice having sterilizing power of the present invention, it is preferable that the interval between the anode plate and the cathode plate is within the range of 2–6 mm.

With this arrangement, the ferrite electrode as the anode plate has sufficient durability even if a high voltage of 10 V or more is imposed thereon. Accordingly, the increase of the interval between the electrodes to 2–6 mm permits a high electrolysis processing capability to be obtained as well as prevents the calcium, magnesium, etc. contained in fresh water such as tap water and the like from being eluted and deposited on the cathode plate as hydroxides and clogging between the electrode plates as much as possible.

In the method of manufacturing ice having sterilizing power of the present invention, it is preferable that the method comprises the steps of electrolyzing the fresh water by circulating it through the electrolyzing passage a plurality of times; and discharging the electrolyzed water to the outside when the free residual halogen concentration of the sterilizing water reaches a prescribed set concentration and freezing the sterilizing water.

With this arrangement, the free residual halogen concentration in the sterilizing water can be increased by repeating the electrolysis many times and ice can be effectively produced by discharging the sterilizing water to the outside.

In the method of manufacturing ice having sterilizing power of the present invention, it is preferable that the method comprises the steps of setting a current supplied between the anode plate and the cathode plate to a prescribed value; detecting a voltage produced between the anode plate and the cathode plate at the time and detecting the electric conductivity of the fresh water supplied to the electrolyzing passage based on the voltage; and electrolyzing the fresh water by increasing the set value of the current when the electric conductivity is low.

When the fresh water to be supplied is specifically tap water, the electric conductivity thereof is not constant and varies depending upon seasons and times. Therefore, when the electric conductivity is lowered, a prescribed free residual halogen concentration having a sufficient sterilizing capability may not be obtained even if the current set to the prescribed value is supplied. With this arrangement, however, when the electric conductivity of the fresh water to be supplied is low, sterilizing and rinsing water having a desired free residual halogen concentration can be stably obtained by increasing the prescribed current value to be supplied.

DESCRIPTION OF THE PREFERRED EMBODIMENT

An embodiment of the present invention will be described below with reference to the accompanying drawings.

Figure 1:
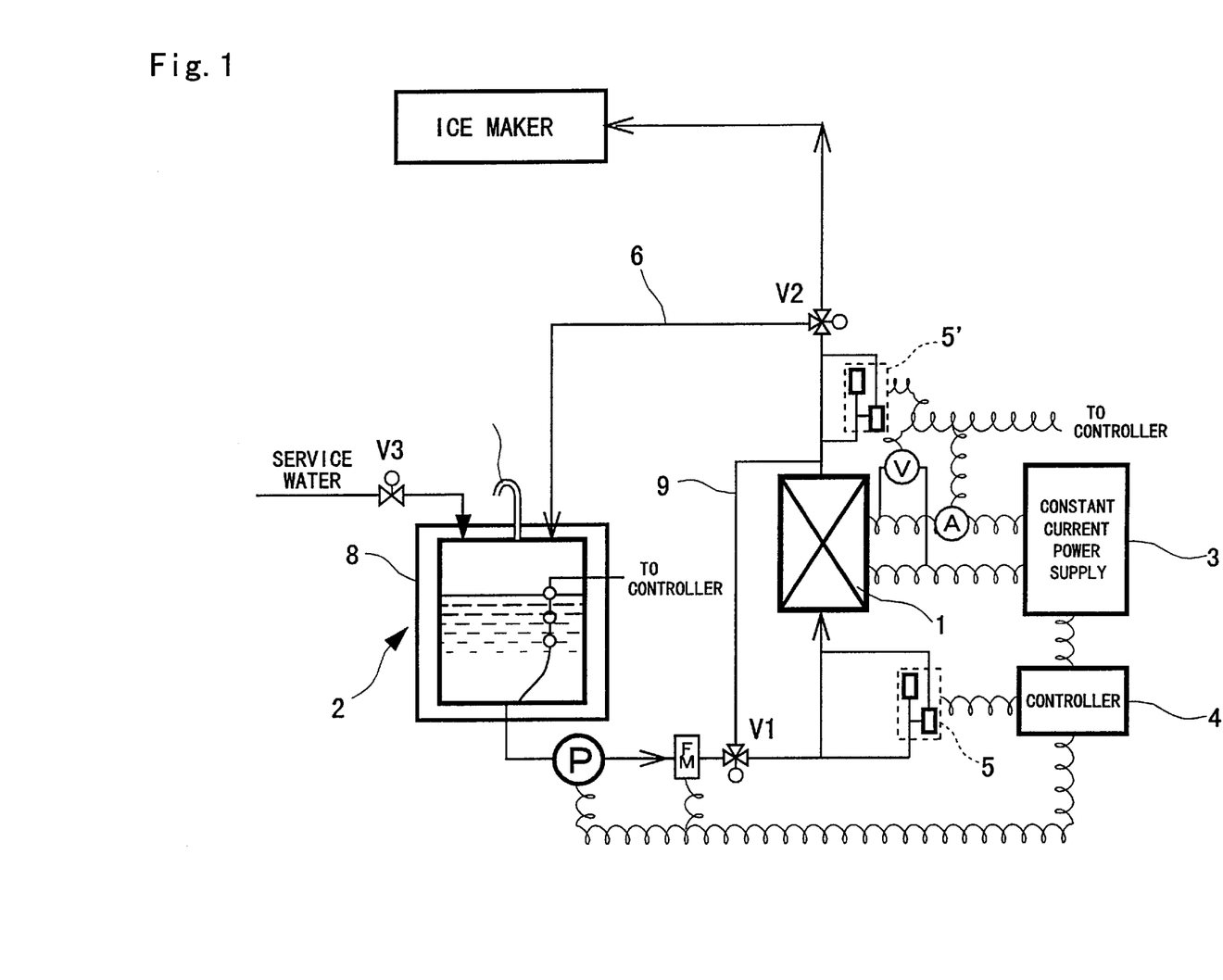
FIG. 1 is a system flow diagram showing a method of manufacturing ice having sterilizing power of an embodiment.
Figure 2:
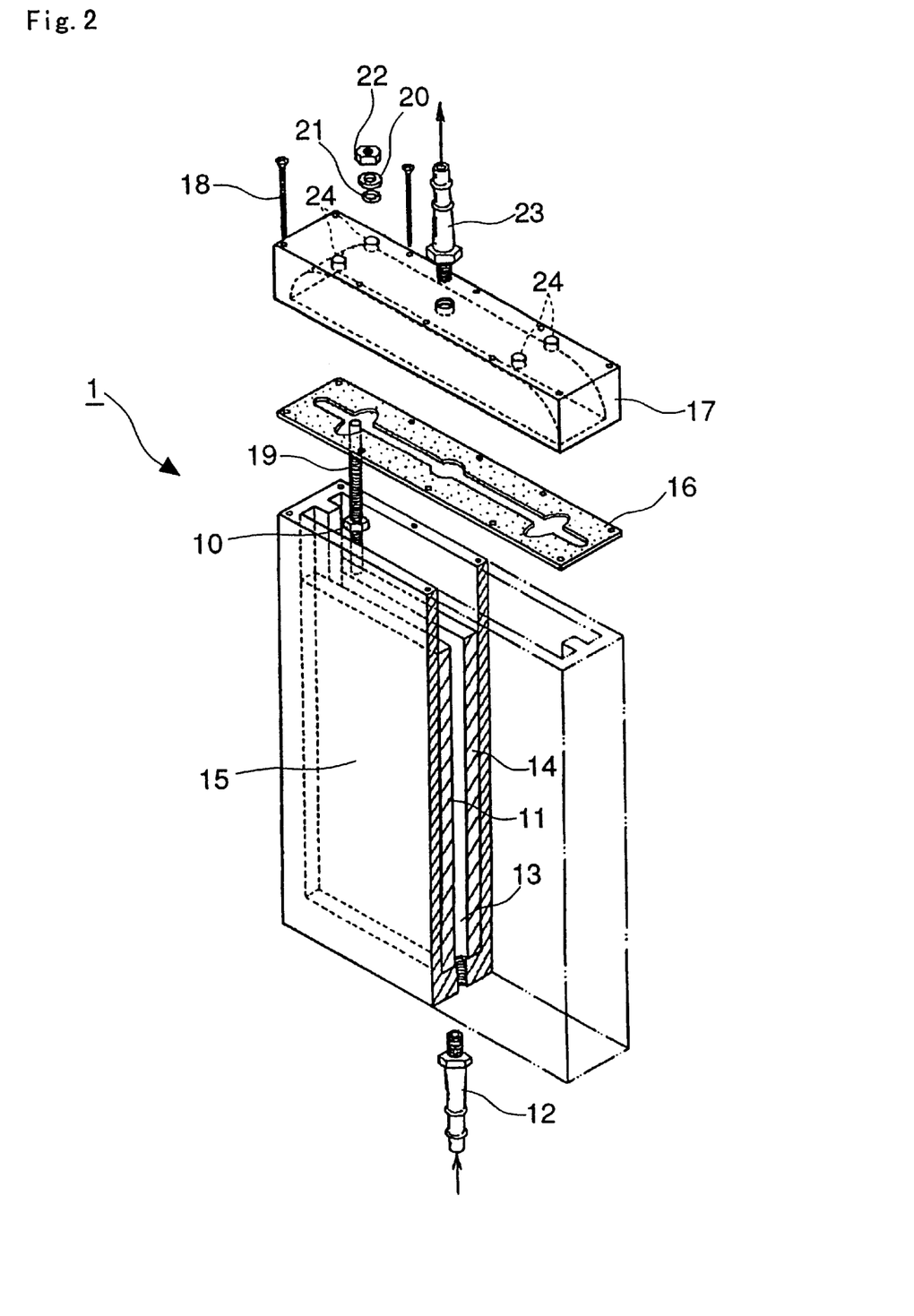
FIG. 2 is an exploded perspective view, partly in cross section, showing the structure of an electrolyzing reaction apparatus using the method of manufacturing the ice having the sterilizing power of the embodiment.
Figure 3:
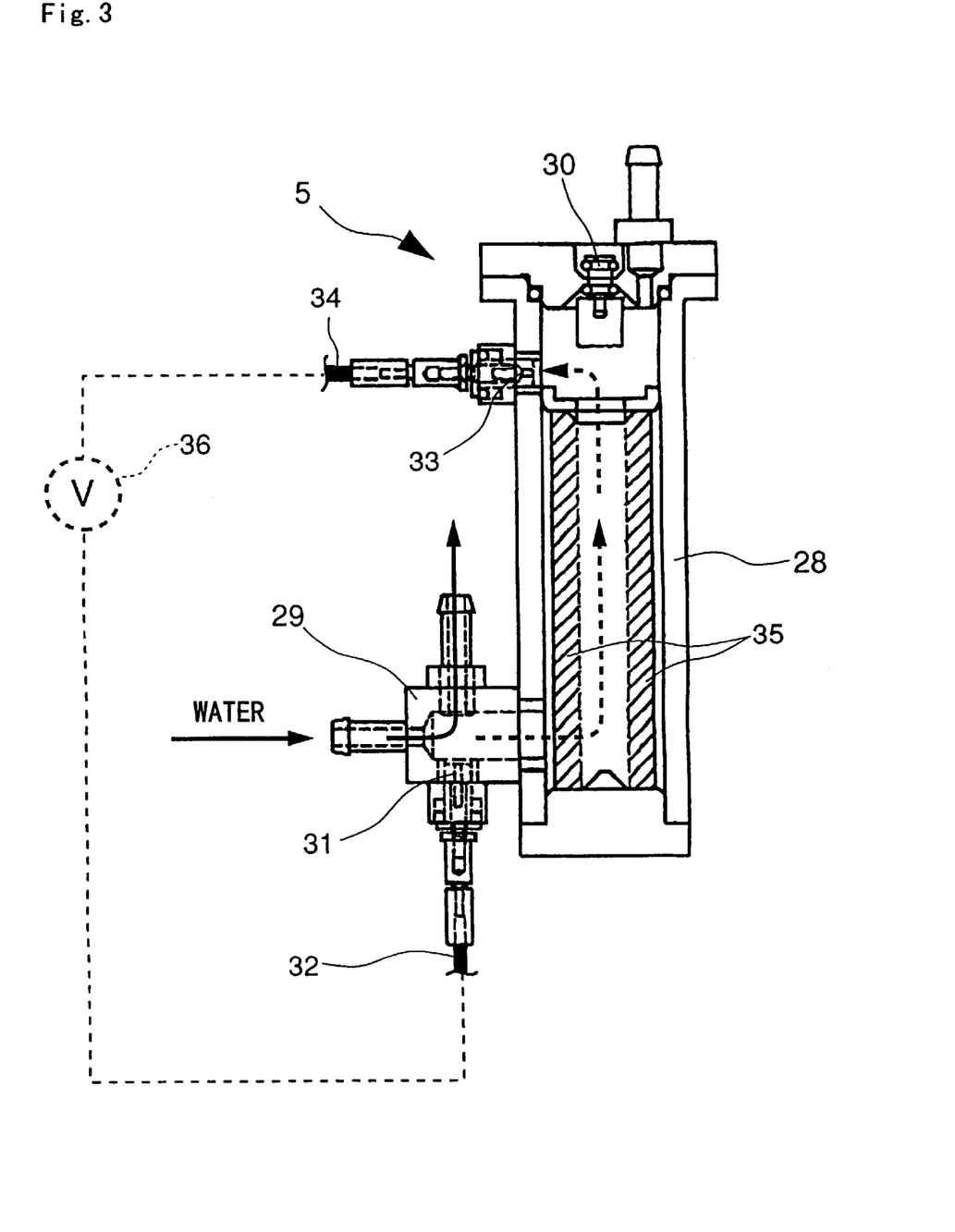
FIG. 3 is a side sectional view showing a residual halogen concentration sensing device used to the method of manufacturing the ice having the sterilizing power of the embodiment.
Figure 4:
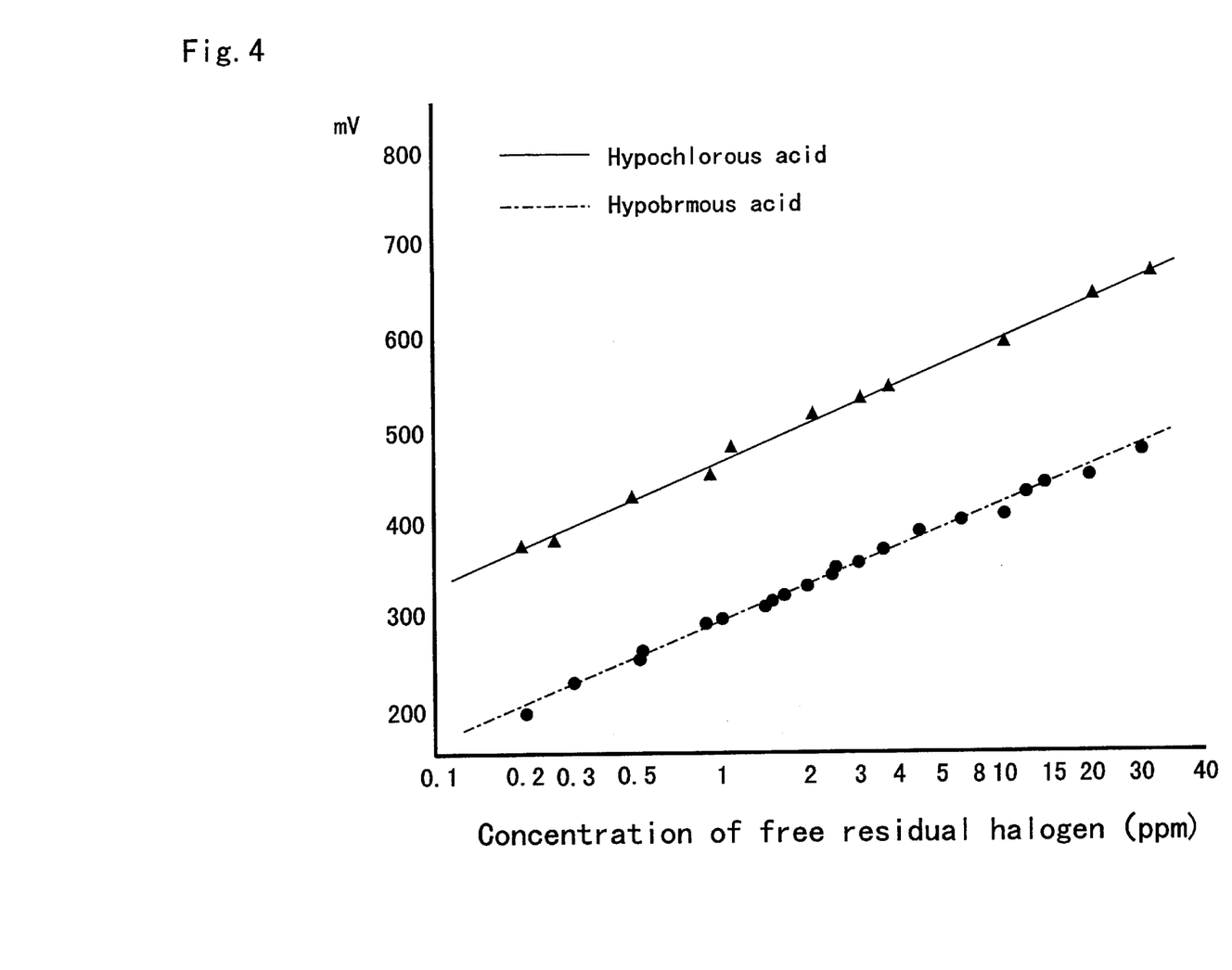
FIG. 4 is a graph showing the relationship between the voltage and the concentrations of hypochlorous acid and hypobromous acid in the residual halogen concentration sensing device.

FIG. 1 is a system flow diagram showing a method of manufacturing ice having sterilizing power of an embodiment, FIG. 2 is an exploded perspective view, partly in cross section, showing the structure of an electrolyzing reaction apparatus using the method of manufacturing the ice having the sterilizing power of the embodiment, FIG. 3 is a side sectional view showing a residual halogen concentration sensing device used to the method of manufacturing the ice having the sterilizing power of the embodiment and FIG. 4 is a graph showing the relationship between the voltage and the concentrations of hypochlorous acid and hypobromous acid in the residual halogen concentration sensing device.

In FIG. 1, LS generally denotes a level sensor for detecting a water level, FM denotes a flow meter, P denotes a pump and V denotes an electromagnetic valve.

As shown in FIG. 1, a system for manufacturing the ice having the sterilizing power of the embodiment is essentially composed of a storage tank 2 in which service water as tap water is temporarily stored, from which the service water is supplied to an electrolyzer 1 by a pump P also serving as a circulating pump and to which the water electrolyzed by the electrolyzer 1 is returned through a return passage 6 and temporarily stored, the circulating pump P disposed in a water passage connected from the storage tank 2 to the electrolyzer 1 and capable of changing its flow rate in response to an indication from a controller 4, a flow meter FM, a residual halogen concentration sensor 5 connected to the water passage connected to the electrolyzer 1 for detecting the free residual halogen concentration of the water supplied to the electrolyzer 1 and a residual halogen concentration sensor 5' connected to a position branched from the electrolyzer 1 downstream thereof for detecting the free residual halogen concentration of the water electrolyzed in the electrolyzer 1, the electrolyzer 1 for electrolyzing the water as the service water or the circulating water supplied from the storage tank 2 by the circulating pump P and producing hypohalogenous acid such as hypochlorous acid, hypobromous acid, etc., a constant current power supply 3 for supplying a current set to a prescribed value to the electrolyzer 1, the controller 4 connected to the circulating pump P, the flow meter FM, the residual halogen concentration sensors 5, 5', the constant current power supply 3 and respective electromagnetic valves V1, V2, V3 and the like and composed of a control substrate and the like for performing the control and the like of the respective components and an ice maker for making ice by freezing the water containing free residual halogen of a prescribed concentration and discharged to the outside. The water passage connected to the downstream side of the electrolyzer 1 is branched to the return passage 6 and a supply passage connected to the ice maker. Further, a bypass 9 is branched from the passage connected to the downstream side of the electrolyzer 1 and an electromagnetic valve V1 is connected to the bypass 9. In addition, an electromagnetic valve V2 is connected to a position where the water passage connected to the downstream side of the electrolyzer 1 is branched. The water from the electrolyzer 1 can be circulated to the storage tank 2 or discharged to the ice maker by opening and closing the electromagnetic valves V1, V2 by the controller 4.

The electrolyzer 1 of the embodiment is arranged as shown in FIG. 2 and has an electrolyzing passage 13 formed between an anode plate 11 and a cathode plate 14 for performing electrolysis.

The anode plate 11 of the embodiment is composed of ferrite and the cathode plate 14 thereof is composed of titanium and the respective electrode plates are inserted into a vinyl chloride cabinet 15 formed to dispose the respective electrode plates at a prescribed interval set to about 6 mm in the embodiment.

It is preferable that the interval between the anode plate 11 and the cathode plate 14 is as large as possible from the viewpoint of throughput. When, however, the interval is large, a voltage imposed between the respective electrode plates is greatly increased because the fresh water such as the service water and the like to be electrolyzed has a low electric conductivity and the cost of a constant current power supply capable of imposing the high voltage becomes expensive, whereas when the imposed voltage is low, the throughput of the electrolyzer 1 is lowered as well as a disadvantage is liable to be caused by hydroxides such as calcium, magnesium, etc. educed to the cathode and deposited thereon. Thus, it is preferable to set the interval to the range of 2–6 mm because the deposits can be removed by a scraper or the like at the time, although it is not provided with the embodiment.

It is preferable that the ferrite electrode used as the anode of the embodiment is composed of nickel simple ferrite obtained by baking nickel oxide as a divalent metal compound, which is mixed with ferric oxide at a prescribed ratio, under suitable atmospheric conditions. This is because that the nickel simple ferrite is excellent in specific resistance, corrosion resistance, shock resistant strength and the like. The embodiment also employs nickel simple ferrite (made by TDK). Two titanium electrode terminals 19 are formed at prescribed positions on the upper surface of the anode plate 11 of the nickel simple ferrite.

Although the anode is composed of the ferrite in the embodiment, the present invention is not limited thereto and graphite may be used likewise the ferrite and further the graphite may be used as the cathode.

It is preferable to form a plurality of the electrode terminals 19 on the electrode plates and in particular on the anode as described above in order to reduce a load on the electrode terminals 19 and other junctions because a high voltage is imposed on the respective electrode plates when fresh water such as tap water, etc. having a low electric conductivity is electrolyzed. The number of the electrode terminals 19 may be more increased.

It is preferable to increase the area of the respective electrode plates because a voltage produced between the respective electrode plates can be lowered by it when a current set to a prescribed value is supplied thereto. However, the ferrite electrode has a problem that it is difficult to form it to a large area because it is deformed in a baking process. Therefore, a multiplicity of ferrite electrodes each having a prescribed area may be connected to each other and electrically conducted so that they can be used as an electrode having a large area.

The opening of the cabinet 15 at an end thereof is closed by a vinyl chloride lid 17 which is fixed thereto by conical screws 18 through a packing 16. The two electrode terminals 19, which are exposed to the outside of the cabinet 15 through the lid 17, are provided with the anode plate 11 and the cathode plate 14 (only one of the electrode terminals 19 connected to the cathode plate 14 is shown). Each of the electrode terminals 19 is fixed to the lid 17 through an O-ring 20, a round washer 21 and a stainless nut 22. A titanium nut 10 is disposed to each of the electrode terminals 19 to cover the portion where the electrode terminal 19 is connected to the electrode. A direct current having a prescribed value is supplied from the constant current power supply 3 to the electrode terminals 19. An inlet joint 12 is disposed to the bottom end of the electrolyzer 1 and an outlet joint 23 is connected to the upper end thereof and they are connected to the electrolyzing passage 13, respectively. Water is supplied from the bottom of the electrolyzer 1.

In the embodiment, the constant current power supply 3 is connected to the electrode terminals 19 and the voltage from the constant current power supply 3 is suitably varied so that the current set to the prescribed value is supplied between the electrode plates. A voltmeter V and an ammeter are interposed between the constant current power supply 3 and the electrode terminals 19 as shown in FIG. 1 and connected to the controller 4 so that the controller 4 can detect the voltage and current imposed on the electrolyzer 1 at any time when necessary and calculate the electric conductivity of the water supplied to the electrolyzer 1.

The embodiment is provided with the two residual halogen concentration sensors 5, 5' and one of them is disposed to the water passage connected to the electrolyzer 1 and the other of them is disposed downstream of the electrolyzer 1.

The residual halogen concentration sensors 5, 5' of the embodiment are arranged as shown in FIG. 3. More specifically, each of them is essentially composed of a cylindrical case 28 having a catalyst 35 disposed in it for decomposing hypohalogenous acid, a measuring electrode 31 disposed to a cross-shaped port 29 so as to expose in the water to be measured and a reference electrode 33 disposed so as to expose in the cylindrical case 28. The measuring electrode 31 and the reference electrode 33 are connected to a potential difference meter 36 through cables 32, 34. Numeral 30 in FIG. 3 denotes an air vent valve.

A principle how and why the residual halogen concentration sensors 5, 5 detect a residual halogen concentration will be simply described. First, the space in the cylindrical case 28 is filled with water containing hypochlorous acid, hypochlorous acid ion and the like.

Since the hypochlorous acid and hypochlorous acid ion in the water are approximately perfectly decomposed by the catalyst 35, the space in the cylindrical case 28 is filled with water which contains almost no hypochlorous acid and hypochlorous acid ion.

The water containing the hypochlorous acid and hypochlorous acid ion flows through the cross-shaped port 29 as shown by a solid arrow so that a small potential difference is produced between the measuring electrode 31 exposed in the flow passage and the reference electrode 33 exposed in the water containing no hypochlorous acid and hypochlorous acid ion. Since the relationship shown in FIG. 4 is established between the potential difference and the concentration of the free residual halogen, the concentration of the free residual halogen in the water can be detected by measuring the potential difference by the potential difference meter 36. The potential difference data measured by the potential difference meter 36 is outputted to the controller 4 so that it can detect the concentration of the free residual halogen in the water at any time when necessary.

As shown in FIG. 1, the exterior of the storage tank 2 of the embodiment is shaded by an external housing 8 for shading light. Numeral 7 in the figure denotes a vent hole 7 for introducing and discharging air into and from the storage tank 2. Light is prevented from being incident on the interior of the storage tank 2 also from the vent hole 7.

The shading of the tank 2 can prevent the hypohalogenous acid contained in the water and the sterilizing and rinsing water stored therein from being decomposed by light. When fresh water and the like are used as shown in the present invention, an amount of hypohalogenous acid produced therefrom is smaller than that produced by a method of electrolyzing water added with electrolytes and an efficiency for producing the hypohalogenous acid is low. Thus, it is important to prevent the decomposition of the hypohalogenous acid having been produced once from the viewpoint of the efficiency of the system itself.

A control program for controlling the operation of the respective units is prestored in the controller 4 and the controller 4 determines the value of the current supplied between the respective electrode plates, the flow rate of the water supplied and circulated by the circulation pump P and the discharge of the water to the ice maker based on the control program.

The operation of embodiment will be described below. First, the controller 4 opens the electromagnetic valve V3 so that service water as tap water is supplied into the storage tank 2. When a prescribed water level is detected by the level sensor LS, the controller 4 closes the electromagnetic valve V3 so that a prescribed amount of the service water is stored in the storage tank 2.

Next, the electromagnetic valve V1 opens the passage to the electrolyzer 1 and the circulating pump P supplies the service water in the storage tank 2 into the electrolyzer 1.

The controller 4 sets a prescribed current value previously described in the control program to the constant current power supply 3. The constant current power supply 3 supplies electric power to the electrolyzer 1 while changing its voltage so that the above current value flows between the electrode plates. With this operation, the electrolyzer 1 electrolyzes the water and produces hypochlorous acid or when the service water contains a slight amount of bromine, the electrolyzer 1 produces hypobromous acid.

The water in which hypohalogenous acid such as hypochlorous acid, hypobromous acid, etc. are produced is discharged from the electrolyzer 1 and supplied to the ice maker. Otherwise, when it is desired to increase the concentration of the free residual halogen in the sterilizing and rinsing water having been produced, the water discharged from the electrolyzer 1 is returned to the storage tank 2 through the return passage 6 opened by the electromagnetic valve V2 for circulation so that the water is electrolyzed a plurality of times.

In the electrolyzing operation executed in the electrolyzer 1, since the decrease or increase of the electric conductivity of the water supplied to the electrolyzer 1 increases or decreases the voltage produced between the respective electrode plates, the decrease or increase of the electric conductivity can be detected by measuring the voltage by the volt meter V at any time when necessary. When the electric conductivity of the water greatly decreases and the voltage measured by the volt meter V exceeds a prescribed voltage, the controller 4 changes the prescribed current value set to the constant current power supply 3 to a larger current value.

When the electric conductivity of the water greatly decreases, a desired free residual halogen concentration may not be obtained even if the prescribed current is supplied. Thus, the above operation is preferable because a stable free residual halogen can be obtained by suppressing the decrease of the free residual halogen as much as possible by setting the prescribed current value to the larger current value and controlling it.

In the embodiment, the controller 4 is also connected to the residual halogen concentration sensor 5' as described above and can detect the free residual halogen concentration of the water produced by the electrolyzer 1 at any time when necessary. When the thus detected free residual halogen concentration of the water is lower than a prescribed concentration, the controller 4 determines that the service water supplied from the storage tank 2 contains electrolytes other than sodium chloride and hypohalogenous acid having the prescribed concentration is not produced. In this case, the current value set to the constant current power supply 3 is increased. If the prescribed concentration cannot be still obtained regardless of the increase of the current value, the circulating amount of the water is reduced by reducing the rotation of the circulating pump P so that the prescribed amount of the free residual halogen concentration can be produced.

The above operation is preferable because it can prevent the prescribed amount of hypohalogenous acid from not being produced and sterilizing and rinsing water having a free residual halogen concentration lower than the prescribed concentration from being supplied when the service water supplied to the electrolyzer 1 contains the electrolytes other than sodium chloride.

Further, when it is desired to make the free residual halogen concentration to a higher concentration, the higher concentration can be obtained by furthermore circulating the water through the return passage 6 and causes the water to pass through the electrolyzer 1 a plurality of times for electrolysis.

The free residual halogen concentration in the water having been circulated as described above is successively increased. When the free residual halogen concentration detected by the residual halogen concentration sensor 5 reaches a discharge concentration preset to a prescribed value, the controller 4 opens the passage to the ice maker through the electromagnetic valve V2 as well as the passage on the bypass 9 side through the electromagnetic valve V1 so that the water containing the free residual halogen made to the prescribed concentration in the storage tank 2 is transferred to the ice maker and made to ice by being frozen.

A specific working example using the sterilizing and rising water generating apparatus of the embodiment will be described below.

(Working example)

Recently, the pollution of foods and drinks and the vessels thereof caused by germs has been investigated because more strict countermeasures for disease-causing germs have been taken since the occurrence of the food poisoning caused by pathogenic *E. coli O*-157. It has been found in the investigation that the surfaces of the vessels for foods and drinks become greatly polluted with germs.

In particular, it has been confirmed that germs are grown and pollution prevails when foods and drinks are delivered while been cooled with ice or the like in packages. The packages for drinks to which straws are attached are supposed to be most dangerous among the packages for food and drinks. The drinks are delivered to respective customers by a truck driver in a state that they are contained in the packages. In April to October, the packages are distributed to respective customers by being put into a carrier bag filled with cubic ices.

An example that the ice having sterilizing power of the present invention was used to the delivery of drink packages to respective customers will be described below.

Tap water having an electric conductivity of 193 $\mu$s/cm and pH 7.2 and containing about 95 ppm of sodium chloride and 0.67 ppm of hypohalogenous acid was used as service water and the flow rate of the water was set to 100 ml/min, an electrolyzer provided with electrodes each having an electrode area of 2 $dm^2$ was used as the electrolyzer 1 and a constant power supply having a capacity of 300 W (upper limit voltage; 50 V) was used as the constant current power supply 3. After sterilizing and rinsing water containing a prescribed free residual halogen concentration (converted into hypochlorous acid) was produced by circulating the water, the thus produced water was supplied to the ice maker through the electromagnetic valve V2 and made to ice. Then, the sterilizing effects of the ices having respective free residual halogen concentrations were tested.

A method of testing the sterilizing power of the ice was performed as described below. Each 100 grams of the ice produced as described above was put into a vessel and the vessel was placed in a thermostat at 32° C.; the volumes of waters made by the melt of the ice were measured every time prescribed periods of time (1 hour, 3 hours, 5 hours and 7 hours in Table 1) had passed; complicatedly processed water containing $8.2\times10^3$ CFU/ml of colon bacilli and $4.1\times10^4$ CFU/ml of ordinary germs was prepared and added to the above respective waters in the amount of 10% of the volumes of the waters; the waters were sampled for a culturing test when one hour elapsed after the addition of the complicatedly processed water.

As a comparative example, ice was made from service water and the same test as above was performed.

As culturing conditions, the ordinary germs were cultured in standard agar culture mediums for 48 hours and the colon bacilli were cultured in desoxycholate agar culture mediums for 24 hours at 37±1° C., respectively and it was assumed that the average number of germs in a plurality of culture plates was the number of the germs.

Figure 5:
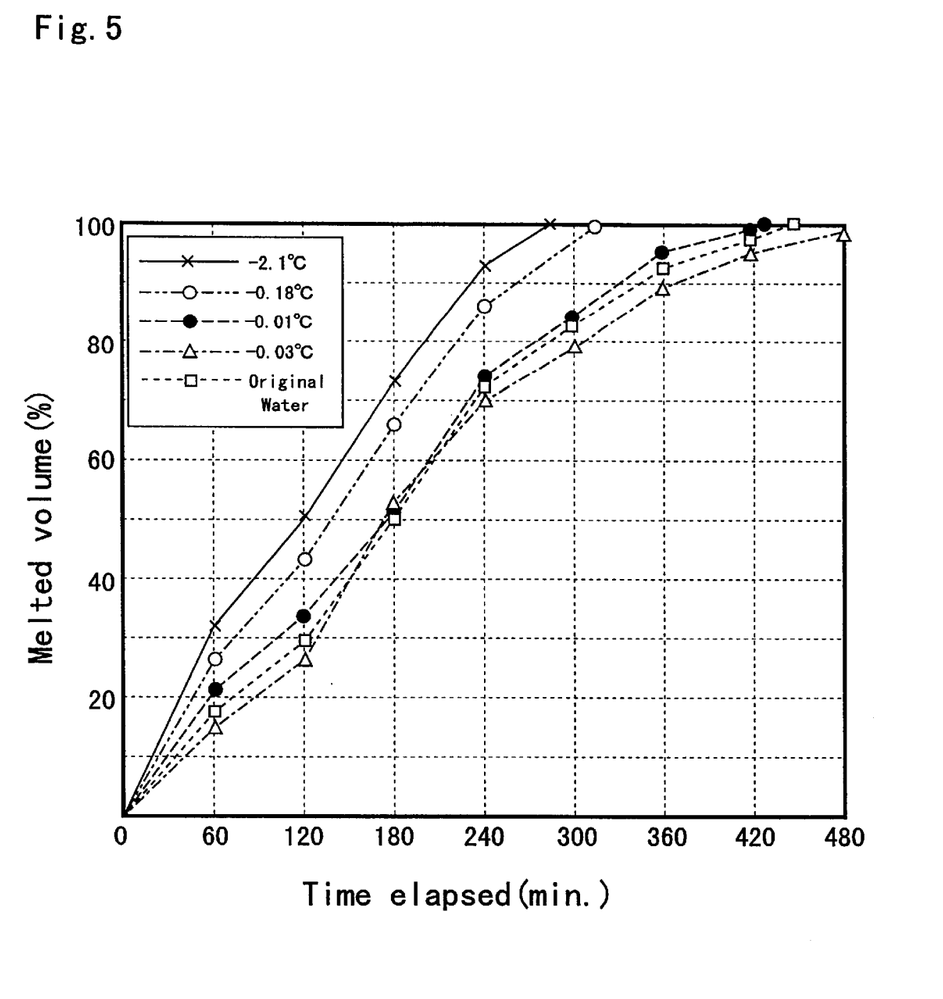
FIG. 5 is a graph showing the relationship between the melting points and the melting speeds of the ice in the embodiment.

The result of the test is as shown in Table 1.

the tap water in the storage tank 2 and sodium chloride aqueous solutions having freezing points dropped to respective prescribed values were prepared; the sodium chloride aqueous solutions were electrolyzed in the electrolyzer 1 to have a free residual halogen concentration of 10 ppm and then made to ices by the above ice maker; and the volumes of the waters obtained from the ice melted in a thermostat set to an atmosphere of 36±1° C. were measured at respective times. FIG. 5 shows the result of the measurement.

TABLE 1

| Type | Concentration of initial free residual chlorine (ppm) | After 1 hour | | After 3 hour | | After 5 hour | | After 7 hour | |
|---|---|---|---|---|---|---|---|---|---|
| | | Concentration of free residual chlorine (ppm) | Number of viable germs (CFU/ml) | Concentration of free residual chlorine (ppm) | Number of viable germs (CFU/ml) | Concentration of free residual chlorine (ppm) | Number of viable germs (CFU/ml) | Concentration of free residual chlorine (ppm) | Number of viable germs (CFU/ml) |
| Group of colon bacilli | | | | | | | | | |
| Ice made from sterilizing water | 10.0 | 9.4 | 0 | 6.4 | 0 | 3.3 | 0 | 2.1 | 0 |
| | 6.0 | 5.2 | 0 | 3.3 | 0 | 1.8 | 0 | 1.1 | 4 |
| | 3.8 | 2.9 | 0 | 1.9 | 0 | 1.2 | 2 | 0.7 | 30 |
| | 2.1 | 1.5 | 0 | 1.0 | 8 | 0.6 | 50 | 0 | $1.8 \times 10^2$ |
| Ice made from tap water | 0.67 | 0 | $2.5 \times 10^2$ | 0 | $4.3 \times 10^2$ | 0 | $6.2 \times 10^2$ | 0 | $8.7 \times 10^2$ |
| Group of ordinary germs | | | | | | | | | |
| Ice made from sterilizing water | 10.0 | 9.4 | 0 | 6.4 | 0 | 3.3 | 0 | 2.1 | 5 |
| | 6.0 | 5.2 | 0 | 3.3 | 0 | 1.8 | 25 | 1.1 | 45 |
| | 3.8 | 2.9 | 0 | 1.9 | 11 | 1.2 | 60 | 0.7 | $1.1 \times 10^2$ |
| | 2.1 | 1.5 | 11 | 1.0 | $1.6 \times 10^2$ | 0.6 | $5.3 \times 10^2$ | 0 | $2.1 \times 10^3$ |
| Ice made from tap water | 0.67 | 0 | $5.6 \times 10^2$ | 0 | $2.6 \times 10^3$ | 0 | $4.7 \times 10^3$ | 0 | $1.8 \times 10^4$ |

Table 1

It is found from the above result that the concentration of the free residual halogen in the water made by the melt of the ice gradually decreases as a time elapses and the colon bacilli and ordinary germs are liable to be increased by the decrease of the concentration of the free residual halogen as the time elapses.

It is preferable that the colon bacilli are negative (not cultured) and the ordinary germs are 10 CFU/ml or less as a safety index of the existence of the colon bacilli and ordinary germs. Since a delivery time of about 7 hours is required to deliver commodities to respective customers in a longest case, it can be found from the above result that about 2 ppm or more of the free residual halogen must remain in the water even after 7 hours elapses in order to satisfy the above condition when 7 hours elapses. Since it can be found that an initial free residual halogen concentration must be 10 ppm or more to make the free residual halogen concentration to 2 ppm or more after 7 hours elapses, it is preferable to set the free residual halogen concentration of the ice having the sterilizing power of the present invention to 10 ppm or more.

Since about 7 hours are required as the delivery time to the respective customers in the longest case as described above, it is sometimes required that the ice having the sterilizing power of the present invention can be used in the state of ice for about 7 hours at the environmental temperature in summer (in the embodiment, an average temperature in summer is set to 36° C. in summer). Thus, how the melting speeds of ices were different depending upon a difference of the melting points thereof was tested.

The melting speeds were tested by the following method. That is, suitable amounts of sodium chloride were added to The amounts of addition of the sodium chloride were set so that sodium chloride concentrations of 3.5%, which corresponded to that of seawater, 0.3% and 500 ppm could be obtained. Further, the melted volume of ice was measured for comparison which was obtained by freezing tap water as original water having a sodium chloride concentration of 120 ppm without adding sodium chloride thereto and without subjecting the water to electrolysis.

As shown in FIG. 5, it can be found that: when the waters having the sodium chloride concentrations of 3.5% and 0.3% are electrolyzed and frozen to ices as performed in the prior art, the ices have high melting speeds and are perfectly melted in 4–5 hours which are shorter than the 7 hours; when the ice having the sodium chloride concentration of 500 ppm and a melting point of −0.03° C. is used, the ice partly remains even after 7 hours elapse, which satisfies the above requirement; and the ice, which is made by directly electrolyzing and freezing the tap water having the sodium chloride concentration of 120 ppm, is not completely melted even after 8 hours elapse and the melting speed thereof is slower than that of the ice made from the original water which is not electrolyzed and thus the ice can be used for a long time in the state of ice.

It is conceived that a reason why the ice subjected to the electrolysis processing can be kept in the state of ice for a time longer than the ice made from the original water is that the magnesium, calcium, etc. contained in the tap water as the original water are eluted to the cathode and removed as described above.

Accordingly, it is preferable that the melting point of the ice having the sterilizing power of the present invention is −0.03° C. or higher as described above.

In this case, when the sterilizing water supplied to the ice maker has a lower sodium chloride concentration, the freezing point of the ice made from the water does not drop and the resulting ice can be maintained in the state of ice for a longer time. However, when the sodium chloride concentration of the water is too low, the water cannot be electrolyzed, whereas when the sodium chloride concentration exceeds 500 ppm, the melting point of the ice made from the water drops and the ice is completely melted in a time shorter than 7 hours. Accordingly, it is preferable that the sodium chloride concentration of the water supplied to the electrolyzer 1 is within the range of 5–500 ppm. Since tap water ordinarily has the sodium chloride concentration within the range of about 20 ppm–200 ppm although it changes depending upon seasons and the like, the tap water may be directly supplied to the electrolyzer 1 as described above.

Figure 6:
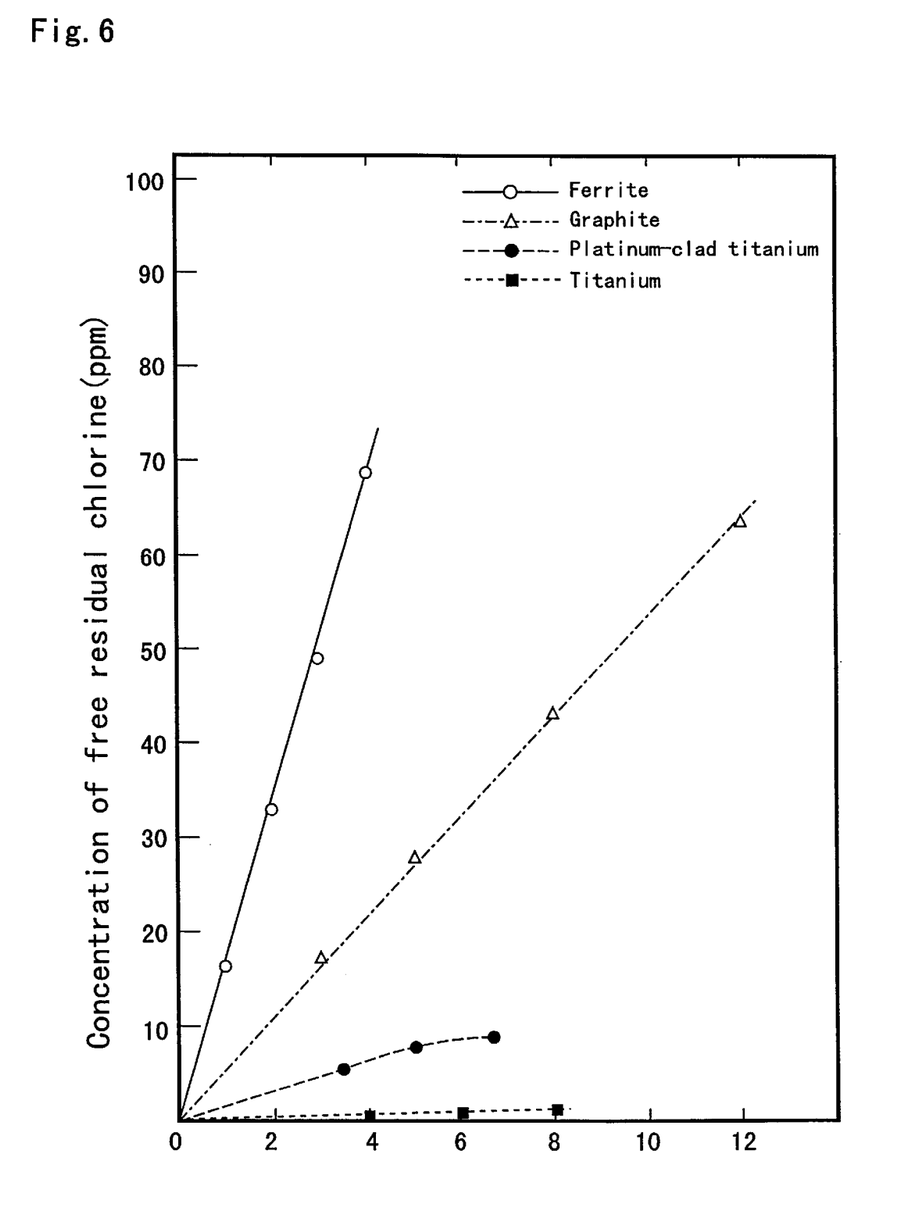
FIG. 6 is a graph showing the relationship between the current values of the respective anode plates and produced hypochlorous acid.

It is found that the free residual halogen concentration of the initial ice is preferably about 10 ppm or more. Thus, a free residual halogen concentration of at least 10 ppm was made by directly electrolyzing fresh water such as the above tap water or the like having a low sodium chloride concentration by the electrolyzer 1 which uses various types of anode plates composed of ferrite, graphite, platinum-clad titanium, and titanium and the hypohalogenous acid producing efficiencies of the respective anode plates were compared with each other by measuring free residual halogen concentrations. FIG. 6 shows a result of measurement.

The free residual halogen concentrations were measured under the comparison conditions that the tap water having an upper limit sodium chloride concentration adjusted to 250 ppm was used as the fresh water, the flow rate of the water was set to 100 ml/min and the area of the respective electrodes plates was set to 2 dm$^2$, and the concentration of the hypohalogenous acid produced by electrolysis processing executed once without circulating the water was measured.

It can be found from the result shown in FIG. 6 that the conventionally used platinum-clad titanium electrode can produce hypochlorous acid at an efficiency higher than that of the titanium electrode, the efficiency of the platinum-clad titanium electrode is low and the electrode cannot produce free residual halogen having a concentration of 10 ppm which is necessary to obtain the above sufficient sterilizing power; on the other hand, since the ferrite electrode and the graphite electrode can obtain free residual halogen having a concentration of 10 ppm or more even if a low current is supplied thereto. Therefore, it is found that the ferrite electrode and the graphite electrode can effectively produce hypochlorous acid because they obtain the free residual halogen of the high concentration even if the low current is supplied thereto. As a result, it is preferable to use the ferrite and graphite as the anode plate used to the electrolyzer 1 for producing the ice having the sterilizing power of the present invention.

While the present invention has been described above in detail, the present invention is by no means limited to the above embodiment and it goes without saying that various changes and additions can be made within the range which does not depart from the gist of the invention.

Although the tap water is used in the embodiment, the present invention is not limited thereto and well water and the like may be used so long as it is fresh water containing sodium chloride of a proper concentration similar to that of the tap water. Further, a slight amount of sodium chloride, sodium bromide, etc. may be added to the fresh water so that the freezing point of it does not increase above –0.03° C.

Although the two residual halogen concentration sensors 5,5' are disposed upstream and downstream of the electrolyzer 1 in the embodiment, the present invention is not limited thereto and only one residual halogen concentration sensor may be disposed. Otherwise, suitable sets of the residual halogen concentration sensors may be disposed at proper positions in the passage.

The present invention will achieve the following advantages.

a) According to a first aspect of the present invention, an excellent sterilizing capability can be obtained by setting the free residual halogen concentration to 10 ppm or more and it can be made difficult for the ice to melt by setting the melting point to –0.03° C. or higher, whereby the ice can be used in the state of ice for a long time.

b) According to a second aspect of the present invention, since hypohalogenous acid is produced by using fresh water containing sodium chloride having a low concentration of 5–500 ppm, the drop of the freezing point of the sterilizing water obtained by the electrolysis can be suppressed to 0.03° C. or less. Accordingly, not only the sterilizing water can be easily made to ice by being frozen but also the ice is made difficult to melt, whereby the ice can be used in the state of ice for a long time.

Further, since the anode plate is composed of ferrite or graphite, a high efficiency for producing hypohalogenous acid and hypohalogenous acid ion can be obtained even from the fresh water having the low sodium chloride concentration as compared with the conventional platinum-clad titanium electrode. Accordingly, sterilizing water can be provided with a prescribed free residual halogen concentration capable of obtaining a sufficient sterilizing capability. Since the sterilizing water has the high hypohalogenous acid and hypohalogenous acid ion producing efficiency, the throughput of an electrolyzer can be increased by increasing the flow rate of the water passing through the electrolyzing passage and the cost of the sterilizing water can be reduced.

c) According to a third aspect of the present invention, the ferrite electrode as the anode plate has sufficient durability even if a high voltage of 10 V or more is imposed thereon. Accordingly, the increase of the interval between the electrodes to 2–6 mm permits a high electrolysis processing capability to be obtained as well as prevents the calcium, magnesium, etc. contained in fresh water such as tap water and the like from being eluted and deposited on the cathode plate as hydroxides and clogging between the electrode plates as mush as possible.

d) According to a fourth aspect of the present invention, the free residual halogen concentration in the sterilizing water can be increased by repeating the electrolysis many times and ice can be effectively produced by discharging the sterilizing water to the outside.

e) When the fresh water to be supplied is specifically tap water, the electric conductivity thereof is not constant and varies depending upon seasons and times. Therefore, when the electric conductivity is lowered, a prescribed free residual halogen concentration having a sufficient sterilizing capability may not be obtained even if the current set to the prescribed value is supplied. According to a fifth aspect of the present invention, however, when the electric conductivity of the fresh water to be supplied is low, sterilizing and rinsing water having a desired free residual halogen concentration can be stably obtained by increasing the prescribed current value to be supplied.

What is claimed is:

1. A method of manufacturing ice having sterilizing power, comprising the steps of:

supplying fresh water containing sodium chloride of a low concentration set to 5–500 ppm and approximately similar to tap water to an electrolyzing passage formed between an anode plate and a cathode plate disposed at a prescribed interval with at least the anode plate composed of a ferrite electrode or a graphite electrode;

electrolyzing the fresh water and making it to sterilizing water having a prescribed free residual halogen concentration; and making ice by freezing the sterilizing water.

2. A method of manufacturing ice having sterilizing power according to claim 1, wherein the interval between said anode plate and said cathode plate is within the range of 2–6 mm.

3. A method of manufacturing ice having sterilizing power according to claim 1 comprising the steps of:

electrolyzing the fresh water by circulating it through said electrolyzing passage a plurality of times; and discharging the electrolyzed water to the outside when the free residual halogen concentration of the sterilizing water reaches a prescribed set concentration and freezing the sterilizing water.

4. A method of manufacturing ice having sterilizing power according to claim 1 comprising the steps of:

setting a current supplied between said anode plate and said cathode plate to a prescribed value;

detecting a voltage produced between said anode plate and said cathode plate at the time and detecting the electric conductivity of the fresh water supplied to said electrolyzing passage based on the voltage; and electrolyzing the fresh water by increasing the set value of the current when the electric conductivity is low.

* * * * *